United States Patent
Gohndrone et al.

(10) Patent No.: US 9,096,622 B2
(45) Date of Patent: Aug. 4, 2015

(54) METHOD OF PRODUCING AN AMINOALKYLALKOXYSILANE

(75) Inventors: John Gohndrone, Midland, MI (US); Joshua Maurer, Bay City, MI (US)

(73) Assignee: Dow Corning Corporation, Midland, MI (US)

( * ) Notice: Subject to any disclaimer, the term of this patent is extended or adjusted under 35 U.S.C. 154(b) by 417 days.

(21) Appl. No.: 13/499,509

(22) PCT Filed: Oct. 7, 2010

(86) PCT No.: PCT/US2010/051726
§ 371 (c)(1),
(2), (4) Date: Mar. 30, 2012

(87) PCT Pub. No.: WO2011/046791
PCT Pub. Date: Apr. 21, 2011

(65) Prior Publication Data
US 2012/0190876 A1    Jul. 26, 2012

Related U.S. Application Data

(60) Provisional application No. 61/252,258, filed on Oct. 16, 2009.

(51) Int. Cl.
 *C07F 7/00* (2006.01)
 *C07F 7/18* (2006.01)
(52) U.S. Cl.
 CPC .................................. *C07F 7/1892* (2013.01)

(58) Field of Classification Search
 CPC ........................................................ C07C 7/0818
 USPC ............................................................ 556/413
 See application file for complete search history.

(56) References Cited

U.S. PATENT DOCUMENTS 4,523,002 A    6/1985  Campbell et al.
5,536,860 A *  7/1996  Monkiewicz et al. ........ 556/413

FOREIGN PATENT DOCUMENTS

| CN | 1746176 A | 3/2006 |
| CN | 101307068 A | 11/2008 |
| GB | 1490720 A | 11/1977 |

OTHER PUBLICATIONS

Speier et al., J. Org. Chem., 36(21);3120-3126.*
Speier J L et al: "Syntheses of (3-aminoalkyl) silicon compounds", Journal of Organic Chemistry, vol. 36, No. 21, Oct. 22, 1971, pp. 3120-3126.

* cited by examiner

*Primary Examiner* — Porfirio Nazario Gonzalez
*Assistant Examiner* — Kofi Adzamli
(74) *Attorney, Agent, or Firm* — Matthew T. Fewkes

(57) ABSTRACT

A method of preparing an aminoalkylalkoxysilane, the method comprising reacting a haloalkylalkoxysilane with ammonia in a high pressure reactor for an amount of time sufficient to consume from 20 to 99.99% (w/w) of the haloalkylalkoxysilane and form an aminoalkylalkoxysilane; venting ammonia from the reactor to give a mixture comprising the aminoalkylalkoxysilane, unreacted haloalkylalkoxysilane, and an ammonium halide; and treating the mixture with a primary amine to form an N-substituted aminoalkylalkoxysilane.

15 Claims, No Drawings

METHOD OF PRODUCING AN AMINOALKYLALKOXYSILANE

CROSS REFERENCE TO RELATED APPLICATIONS

This application is a U.S. national stage filing under 35 U.S.C. §371 of PCT Application No. PCT/US10/51726 filed on Oct. 07, 2010 currently pending, which claims the benefit of U.S. Provisional Patent Application No. 61/252258 filed Oct. 16, 2009 under 35 U.S.C. §119 (e). PCT Application No. PCT/US10/51726 and U.S. Provisional Patent Application No. 61/252258 are hereby incorporated by reference.

FIELD OF THE INVENTION

The present invention relates to a method of preparing an aminoalkylalkoxysilane and more particularly to a method comprising reacting a haloalkylalkoxysilane with ammonia to form an aminoalkylalkoxysilane; venting ammonia from the reactor to give a mixture comprising the aminoalkylalkoxysilane, unreacted haloalkylalkoxysilane, and an ammonium halide; and treating the mixture with a primary amine to form an N-substituted aminoalkylalkoxysilane.

BACKGROUND OF THE INVENTION

Methods of preparing aminoalkylalkoxysilanes are well known in the art. For example, aminoalkylalkoxysilanes can be produced by the aminolysis of haloalkylalkoxysilanes with excess ammonia under high pressure. However, even with a large excess of ammonia, a prolonged period of time, for example, 12 to 15 hours, is required for completion of the reaction with approximately 70% of the reaction time used to consume the last 10% (w/w) of the haloalkylalkoxysilane. Moreover, during the later stage of the reaction, significant amounts of unwanted bis and tris-amine byproducts are formed due to reaction of the aminoalkylalkoxysilane product with the haloalkylalkoxysilane starting material, reducing the yield of the desired product. When the reaction is carried out for shorter periods of time, separation of the aminoalkylalkoxysilane product from the unreacted haloalkylalkoxysilane is both difficult and costly to achieve on a commercial scale, as these compounds have similar boiling points. Consequently, there is a need for a method of preparing aminoalkylalkoxysilanes by aminolysis of haloalkylalkoxysilanes that minimizes reaction time, reduces byproduct formation, and avoids separation of starting material and product.

SUMMARY OF THE INVENTION

The present invention is directed to a method of preparing an aminoalkylalkoxysilane, the method comprising:

(i) reacting a haloalkylalkoxysilane having the formula $X(CH_2)_m SiR^1_n(OR^1)_{3-n}$ (I) or

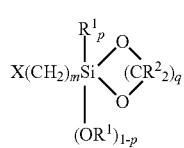
(II)

with ammonia in a high pressure reactor at a temperature from 30 to 200° C. and for an amount of time sufficient to consume from 20 to 99.99 weight % of the haloalkylalkoxysilane and form an aminoalkylalkoxysilane, wherein each $R^1$ is independently selected from $C_1$-$C_{10}$ hydrocarbyl, each $R^2$ is independently selected from —H and $C_1$-$C_4$ hydrocarbyl, m is 1, 2, 3, 4, 5 or 6, n is 0, 1, or 2, p is 0 or 1, q is 2, 3, 4, or 5, and X is halo;

(ii) venting ammonia from the reactor to give a mixture comprising the aminoalkylalkoxysilane, unreacted haloalkylalkoxysilane, and an ammonium halide; and (iii) treating the mixture with a primary amine having a boiling point of at least 115° C. such that the primary amine reacts with the unreacted haloalkylakoxysilane to form an N-substituted aminoalkylalkoxysilane.

The method of the invention produces aminoalkylalkoxysilanes by the aminolysis of haloalkylalkoxysilanes, minimizes reaction time, reduces byproduct formation, and avoids separation of starting material and product. Moreover, the method produces aminoalkylalkoxysilanes of high purity. Further, the method produces commercially useful N-substituted aminoalkylalkoxysilanes. Still further, the method produces an N-substituted aminoalkylalkoxysilane that is easily separated from the aminoalkylalkoxysilane.

The aminoalkylalkoxysilane product of the present method can be used as a coupling agent for thermoset and thermoplastic resins with glass or mineral fillers.

DETAILED DESCRIPTION OF THE INVENTION

As used herein, "a" and "an" are intended to mean one or more.

A method of preparing an aminoalkylalkoxysilane according to the present invention comprises:

(i) reacting a haloalkylalkoxysilane having the formula $X(CH_2)_m SiR^1_n(OR^1)_{3-n}$ (I) or

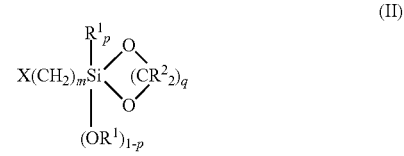
(II)

with ammonia in a high pressure reactor at a temperature from 30 to 200° C. and for an amount of time sufficient to consume from 20 to 99.99% (w/w) of the haloalkylalkoxysilane and form an aminoalkylalkoxysilane, wherein each $R^1$ is independently selected from $C_1$-$C_{10}$ hydrocarbyl, each $R^2$ is independently selected from —H, and $C_1$-$C_4$ hydrocarbyl, m is 1, 2, 3, 4, 5 or 6, n is 0, 1, or 2, p is 0 or 1, q is 2, 3, 4, or 5, and X is halo;

(ii) venting ammonia from the reactor to give a mixture comprising the aminoalkylalkoxysilane, unreacted haloalkylalkoxysilane, and an ammonium halide; and (iii) treating the mixture with a primary amine having a boiling point of at least 115° C. such that the primary amine reacts with the unreacted haloalkylakoxysilane to form an N-substituted aminoalkylalkoxysilane.

In step (i) of preparing the aminoalkylalkoxysilane, a haloalkylalkoxysilane having the formula $X(CH_2)_m SiR^1_n (OR^1)_{3-n}$ (I) or

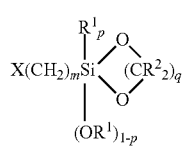

is reacted with ammonia in a high pressure reactor at a temperature from 30 to 200° C. and for an amount of time sufficient to consume from 20 to 99.99% (w/w) of the haloalkylalkoxysilane and form an aminoalkylalkoxysilane, wherein each $R^1$ is independently selected from $C_1$-$C_{10}$ hydrocarbyl, each $R^2$ is independently selected from —H and $C_1$-$C_4$ hydrocarbyl, m is from 1 to 6, n is 0, 1, or 2, p is 0 or 1, q is 2, 3, 4 or 5, and X is halo.

The haloalkylalkoxysilane has the formula $X(CH_2)_m SiR^1_n (OR^1)_{3-n}$ (I) or

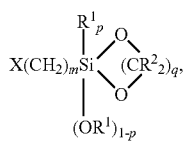

wherein each $R^1$ is independently selected from $C_1$-$C_{10}$ hydrocarbyl, $R^2$ is selected from $C_1$-$C_4$ hydrocarbyl, m is 1, 2, 3, 4, 5 or 6, n is 0, 1, or 2, p is 0 or 1, q is 2, 3, 4 or 5, and X is halo. Examples of halo atoms represented by X include —F, —Cl, —Br, and —I.

The hydrocarbyl groups represented by $R^1$ typically have from 1 to 10 carbon atoms, alternatively from 1 to 6 carbon atoms, alternatively from 1 to 4 carbon atoms. Acyclic hydrocarbyl groups containing at least three carbon atoms can have a branched or unbranched structure. Examples of hydrocarbyl groups include, but are not limited to, alkyl, such as methyl, ethyl, propyl, 1-methylethyl, butyl, 1-methylpropyl, 2-methylpropyl, 1,1-dimethylethyl, pentyl, 1-methylbutyl, 1-ethylpropyl, 2-methylbutyl, 3-methylbutyl, 1,2-dimethylpropyl, 2,2-dimethylpropyl, hexyl, heptyl, octyl, nonyl, and decyl; cycloalkyl, such as cyclopentyl, cyclohexyl, and methylcyclohexyl; aryl, such as phenyl and napthyl; alkaryl such as tolyl and xylyl; aralkyl, such as benzyl and phenylethyl; alkenyl, such as vinyl, allyl, and propenyl; aralkenyl, such as styryl and cinnamyl; and alkynyl, such as ethynyl and propynyl.

The hydrocarbyl groups represented by $R^2$ typically have from 1 to 4 carbon atoms, alternatively from 1 to 2 carbon atoms. Acyclic hydrocarbyl groups containing at least three carbon atoms can have a branched or unbranched structure. Examples of hydrocarbyl groups include, but are not limited to, alkyl, such as methyl, ethyl, propyl, 1-methylethyl, butyl, 1-methylpropyl, 2-methylpropyl, and 1,1-dimethylethyl.

The subscripts m, n, p, and q are integers. The subscript m typically has a value of from 1 to 6, alternatively 2 to 4, alternatively 3; the subscript n typically has a value of from 0 to 2, alternatively 0 or 1; the subscript p typically has a value of 0 or 1, alternatively 0; the subscript q typically has a value from 2 to 5, alternatively 2 to 4, alternatively 2.

Examples of haloalkylalkoxysilanes include, but are not limited to, haloalkylalkoxysilanes having the formulae: $Cl(CH_2)_3Si(OCH_3)_3$, $Cl(CH_2)_3Si(CH_3)(OCH_3)_2$, $Cl(CH_2)_3 Si(CH_3)_2(OCH_3)$, $Cl(CH_2)_3Si(OCH_2CH_3)_3$, $Cl(CH_2)_3Si(CH_3)(OCH_2CH_3)_2$, $Cl(CH_2)_3Si(CH_3)_2(OCH_2CH_3)$, $Br(CH_2)_3Si(OCH_3)_3$, $Br(CH_2)_3Si(CH_3)(OCH_3)_2$, $Br(CH_2)_3Si(CH_3)_2(OCH_3)$, $Br(CH_2)_3Si(OCH_2CH_3)_3$, $Br(CH_2)_3Si(CH_3)(OCH_2CH_3)_2$, $Br(CH_2)_3Si(CH_3)_2(OCH_2CH_3)$, $I(CH_2)_3Si(OCH_3)_3$, $I(CH_2)_3Si(CH_3)(OCH_3)_2$, $I(CH_2)_3Si(CH_3)_2(OCH_3)$, $I(CH_2)_3Si(OCH_2CH_3)_3$, $I(CH_2)_3Si(CH_3)(OCH_2CH_3)_2$, $I(CH_2)_3Si(CH_3)_2(OCH_2CH_3)$,

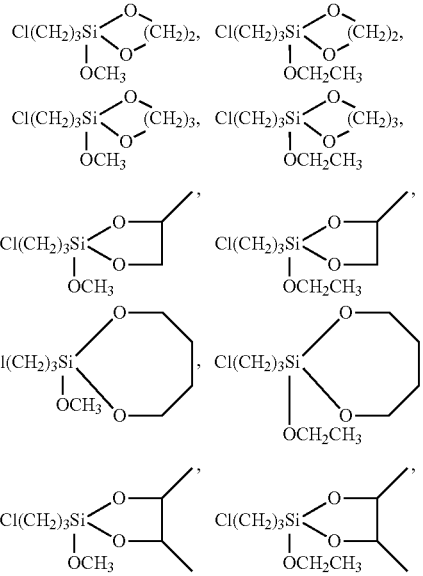

Methods of preparing haloalkylalkoxysilanes are well known in the art; many of these compounds are commercially available. The haloalkylalkoxysilanes may be made by the reaction of the appropriate haloalkylhalosilane with an alcohol. They also may be made by the reaction of an haloalkylalkoxysilane with an alkanediol under suitable conditions. Alcohols used to make the haloalkylalkoxysilane are, for example, methanol, ethanol, propanol and butanol. Diols used to make the haloalkylalkoxysilane are, for example, 1,2-ethanediol, 1,2-propanediol, 1,3-propanediol, 1,4-butanediol, and 2-iso-butyl-1,4-butanediol.

The ammonia is liquid ammonia in equilibrium with gaseous ammonia at the temperature and pressure of the reaction. Liquid ammonia is commercially available.

The reaction of the haloalkylalkoxysilane and ammonia to produce the aminoalkylalkoxysilane can be carried out in any standard high-pressure reactor suitable for contacting, for example, haloalkylalkoxysilanes with ammonia. Suitable reactors include high-pressure Parr reactors, autoclaves, and tumbling autoclaves. Preferably, the reactor is equipped with a means of agitation, such as stirring.

The haloalkylalkoxysilane and ammonia may be combined in any order. Typically, the ammonia and haloalkylalkoxysilane are added to the reactor simultaneously or almost simultaneously at ambient temperature; however, either the ammonia or haloalkylalkoxysilane may be added first followed by the other.

There is no particular rate of addition to the reactor of either the ammonia or the haloalkylalkoxysilane. The ammonia and haloalkylalkoxysilane are typically metered into the reactor, then the reactor is heated to drive the reaction.

The reaction of the ammonia and the haloalkylalkoxysilane is typically carried out at a temperature from 30 to 200° C., alternatively from 30 to 150° C., alternatively from 30 to 110° C. The reaction temperature is increased through the use of suitable equipment such as a reactor steam jacket or heating mantle.

The time of reaction of the ammonia and the haloalkylalkoxysilane depends upon the temperature and the consumption of the haloalkylalkoxysilane. The reaction is carried out for an amount of time sufficient to consume from 20 to 99.99% (w/w) of the haloalkylalkoxysilane, alternatively 40 to 99.99% (w/w), alternatively from 70 to 99.98% (w/w), alternatively 85 to 99.98% (w/w). As used herein, "consume" means that the haloalkylalkoxysilane has reacted to form a compound, such as the aminoalkylalkoxysilane described below, different than the haloalkylalkoxysilane. The rate at which the haloalkylalkoxysilane is consumed increases with increasing temperature. The reaction time is typically from 0.5 to 15 hours, alternatively from 0.5 to 12 hours, alternatively from 0.5 to 2.5 hours, at a temperature from 70 to 110° C. The quantity of haloalkylalkoxysilane consumed can be determined by assaying the reaction mixture during the method for haloalkylalkoxysilane using common techniques known in art.

The pressure of the reaction between the ammonia and the haloalkylalkoxysilane depends on the temperature. The pressure increases with increasing reaction temperature. The gauge pressure is typically from 1300 to 10300 kPa, alternatively from 2000 to 8,000 kPa, and alternatively 2800 to 6900 kPa, at a reaction temperature from 30 to 110° C.

The ammonia and haloalkylalkoxysilane are typically reacted in a mole ratio of ammonia to haloalkylalkoxysilane of from 10:1 to 100:1, alternatively, from 20:1 to 60:1, alternatively, from 20:1 to 40:1.

In step (ii) of preparing the aminoalkylalkoxysilane, the ammonia is vented from the reactor to give a mixture comprising the aminoalkylalkoxysilane, unreacted haloalkylalkoxysilane, and an ammonium halide.

The temperature at which the ammonia is vented from the reactor is typically about room temperature, although the venting can be conducted at temperatures above room temperature. Techniques known in the art for venting ammonia from a high pressure reactor may be used.

In step (iii) of preparing the aminoalkylalkoxysilane, the mixture is treated with a primary amine having a boiling point of at least 115° C. such that the primary amine reacts with the unreacted haloalkylalkoxysilane to form an N-substituted aminoalkylalkoxysilane. As used herein, "treating" or "treated" means to bring the primary amine and mixture together such that the primary amine will react with the unreacted haloalkylalkoxysilane in the mixture. "Primary amine" means a compound having a nitrogen atom with one organic group and two hydrogen atoms bonded to it. The primary amine may be a monoamine, diamine, triamine, tetramine, or pentamine; alternatively, the primary amine has the formula $H_2N(-R^3NH-)_cH$, wherein each $R^3$ is independently hydrocarbylene and c is 1, 2, 3, or 4, or the formula $H_2NR^4$, wherein $R^4$ is hydrocarbyl.

The hydrocarbylene groups represented by $R^3$ typically have from 2 to 6 carbon atoms, alternatively from 1 to 4 carbon atoms, alternatively from 2 to 4 carbon atoms. Furthermore, the free valences of the hydrocarbylene group are typically separated by 2, 3, or 4 carbon atoms, alternatively 2 or 3 carbon atoms. Examples of hydrocarbylene groups represented by $R^3$ include, but are not limited to, $-CH_2CH_2-$, $-CH_2CH_2CH_2-$, $-CH_2CH(CH_3)-$, $-CH_2(CH_2)_2CH_2-$, $-CH_2(CH_2)_3CH_2-$, $-C(CH_3)_2CH_2CH_2CH_2-$, o-phenylene, p-phenylene, $-C(CH_3)_2CH_2CH(CH_3)-$, and $-CH_2CH(CH_3)CH(CH_2CH_3)-$.

The hydrocarbyl groups represented by $R^4$ typically have from 6 to 20 carbon atoms, alternatively 6 to 12 carbon atoms, alternatively 6 to 10 carbon atoms. Acyclic hydrocarbylene groups can have a branched or unbranched structure. Examples of hydrocarbyl groups include, but are not limited to, alkyl, such as hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl; cycloalkyl, such as cyclohexyl, and methylcyclohexyl; aryl, such as phenyl and napthyl; alkaryl such as tolyl and xylyl; aralkyl, such as benzyl and phenylethyl; alkenyl, such as hexenyl; aralkenyl, such as styryl and cinnamyl; and alkynyl, such as hexynyl.

The subscript c is typically an integer from 1 to 4, alternatively 1 to 3, alternatively 1 or 2.

The boiling point of the primary amine is at least 115° C. For example, the boiling point of the primary amine is from 115 to 400° C., alternatively from 115 to 250° C. The boiling point of the primary amine is selected so that the boiling point of the N-substituted aminoalkylalkoxysilane is sufficiently different than that of the aminoalkylalkoxysilane to allow for separation.

Examples of primary amines include, but are not limited to, ethylenediamine, diethylenetriamine, tetraethylenepentamine, cyclohexylamine, aniline, and benzylamine. In one embodiment, the primary amine is ethylenediamine, cyclohexylamine, or aniline. The primary amine can be a single primary amine or a mixture comprising two or more different primary amines. Further, methods of preparing primary amines are well known in the art; many of these compounds are commercially available. For example, ethylenediamine, cyclohexylamine, aniline and benzylamine, are commercially available.

The primary amine and the mixture may be combined in a batch or continuous process, in a traditional reactor, in a pipe or conduit leading to another process step and equipment, or in the high pressure reactor used in step (i). Reaction vessels, equipment, and methods of combining that are known in the art for the production of N-substituted aminoalkylalkoxysilanes may be used. Preferably, the reactor is equipped with means of agitation, such as stirring, and heating, such as a heating jacket or mantle. The primary amine and mixture may be combined in air or any other typical atmosphere for forming an N-substituted amine from a haloalkylalkoxysilane.

The mixture and the primary amine may be combined in any order. Typically, the primary amine and mixture are combined by adding the primary amine to the mixture; however, reverse addition (i.e., the addition of the mixture to the primary amine) is also possible.

The rate of addition of the primary amine to the mixture or of the mixture to the primary amine is not critical to the reaction of the primary amine to consume the residual haloalkylalkoxysilane. The primary amine may be added to the mixture all at once or over time. Typically, the primary amine is added to the mixture over a few seconds up to 60 minutes at temperatures above 100° C.

The mixture is typically treated with the primary amine at a temperature from 20 to 200° C., alternatively from 40 to 160° C., alternatively from 50 to 150° C.

The amount of time that the mixture is treated with the primary amine depends on several factors, including the structure of the primary amine and the temperature. The mixture is typically treated with the primary amine for up to 24 hours, alternatively from 1 minute to 4 hours, alternatively from 5 minutes to 2.5 hours, at a temperature from 20 to 150°

C. The optimum treatment time can be determined by routine experimentation using the methods set forth in the Examples section below.

The concentration of the primary amine is typically sufficient to effect reaction with the haloalkylalkoxysilane in the mixture. For example, the concentration of the primary amine is typically from 0.5 to 40 moles, alternatively, 1 to 30 moles, alternatively from 2 to 20 moles, per mole of the haloalkylalkoxysilane in the mixture.

The method can further comprise removing ammonium halide from the aminoalkylalkoxysilane. The ammonium halide is typically removed by filtration; however, other methods of removal, such as centrifugation, are also contemplated. Removal of ammonium halide may be conducted at atmospheric pressure, or vacuum or pressure filtration may be employed. Removal is typically after step (ii), step (iii), or step (ii) and (iii). When removed after step (iii), halide salts of the primary amine formed from the hydrogen halide produced in the method and excess primary amine may also be removed.

Further, the aminoalkylalkoxysilane and N-substituted aminoalkylalkoxysilane may also be mixed with a non-polar solvent to precipitate salts, such as ammonium halide, and to drive these salts into the primary amine phase during phase separation as described below. When used, the mass of non-polar solvent is typically from 0.3 to 2 times the mass of the product phase. The non-polar solvent may be any non-polar solvent which causes the precipitation of halide salts formed in the method. Examples of non-polar solvents are linear, branched and cyclic $C_5$-$C_{10}$ alkane, such as pentane, hexane, heptane, octane, nonane, decane and their isomers. The mixing with the non-polar solvent can be carried out with conventional methods, such as shaking or stirring.

The method can further comprise recovering the aminoalkylalkoxysilane and the N-substituted aminoalkylalkoxysilane. After step (iii), the aminoalkylalkoxysilane and the N-substituted aminoalkylalkoxysilane can be recovered by separating the product phase comprising the aminoalkylalkoxysilane and the N-substituted aminoalkylalkoxysilane from the primary amine phase. The separation can be carried out by discontinuing agitation, allowing separation into two layers, and removing the product or primary amine phase.

The aminoalkylalkoxysilane and N-substituted aminoalkylalkoxysilane may then be separated and/or purified. The separation/purification may be conducted using suitable separation/purification techniques such as distillation. The separation/purification may be repeated using a series of distillation systems or recycled back to the same system for subsequent purification and/or separation.

The aminoalkylalkoxysilane prepared according to the present method typically has the formula $H_2N(CH_2)_m SiR^1_n (OR^1)_{3-n}$ (III) or (IV)

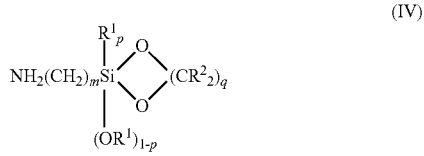

wherein each $R^1$ is independently selected from $C_1$-$C_{10}$ hydrocarbyl, each $R^2$ is independently selected from —H and $C_1$-$C_4$ hydrocarbyl, m is 1, 2, 3, 4, 5 or 6, n is 0, 1, or 2, p is 0 or 1, and q is 2, 3, 4 or 5.

The hydrocarbyl groups represented by $R^1$ and $R^2$ and the subscripts m, n, p, and q are as described and exemplified above for the haloalkylalkoxysilane.

Examples of aminoalkylalkoxysilanes that can be prepared by the present method include, but are not limited to, aminoalkylalkoxysilanes having the formulae: $H_2N(CH_2)_3Si(OCH_3)_3$, $H_2N(CH_2)_3Si(CH_3)(OCH_3)_2$, $H_2N(CH_2)_3Si(CH_3)_2(OCH_3)$, $H_2N(CH_2)_3Si(OCH_2CH_3)_3$, $H_2N(CH_2)_3Si(CH_3)(OCH_2CH_3)_2$, $H_2N(CH_2)_3Si(CH_3)_2(OCH_2CH_3)$, $H_2N(CH_2)_2Si(CH_2CH_3)(OCH_3)_2$, $H_2N(CH_2)_3Si(CH_2CH_3)_2(OCH_3)$, $H_2N(CH_2)_3Si(CH_2CH_3)(OCH_2CH_3)_2$, $H_2N(CH_2)_3Si(CH_2CH_3)_2(OCH_2CH_3)$, $H_2N(CH_2)_3Si(OCH_2CH_3)_3$, $H_2N(CH_2)_3Si(CH_3)(OCH_2CH_3)_2$, $H_2N(CH_2)_3Si(CH_3)_2(OCH_2CH_3)$, $H_2N(CH_2)_4Si(OCH_3)_3$, $H_2N(CH_2)_4Si(CH_3)(OCH_3)_2$, $H_2N(CH_2)_4Si(CH_3)_2(OCH_3)$, $H_2N(CH_2)_4Si(OCH_2CH_3)_3$, $H_2N(CH_2)_4Si(CH_3)(OCH_2CH_3)_2$, $H_2N(CH_2)_4Si(CH_3)_2(OCH_2CH_3)$,

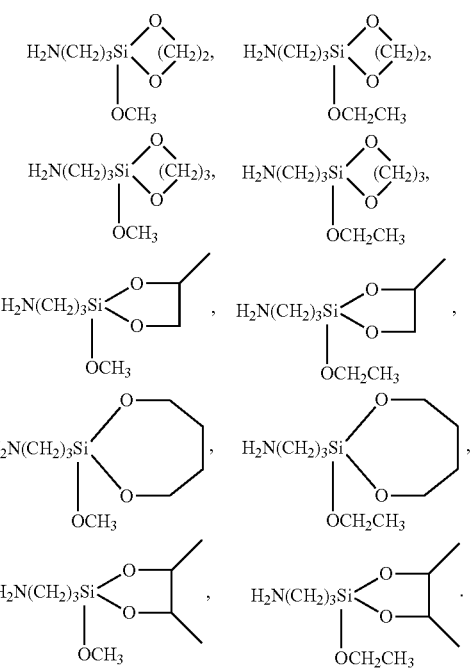

The N-substituted aminoalkylalkoxysilane prepared according to the present method typically has the formula $YNH(CH_2)_m SiR^1_n (OR^1)_{3-n}$ (V) or (VI)

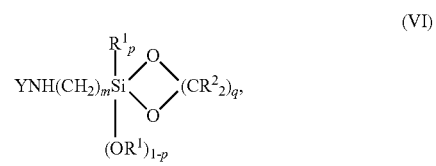

wherein each $R^1$ is independently selected from $C_1$-$C_{10}$ hydrocarbyl, each $R^2$ is independently selected from —H and $C_1$-$C_4$ hydrocarbyl, m is 1, 2, 3, 4, 5 or 6, n is 0, 1, or 2, p is 0 or 1, q is 2, 3, 4, or 5 and Y is —$R^3NH(—R^3NH—)_c H$ or $R^4$, wherein $R^3$ is hydrocarbylene, $R^4$ is hydrocarbyl, and c is 0, 1, 2, or 3.

The hydrocarbyl groups represented by $R^1$ and $R^2$ and the subscripts m, n, p, and q are as described and exemplified above for the haloalkylalkoxysilane. The hydrocarbyl groups represented by $R^4$ and the hydrocarbylene groups represented by $R^3$ are as described and exemplified above for the primary amine.

The subscript c is an integer typically from 0 to 3, alternatively 0 to 2, alternatively 0 or 1.

The N-substituted aminoalkylalkoxysilane has a boiling point which is different than the boiling point of the aminoalkylalkoxysilane. For example, the boiling point of the N-substituted aminoalkylalkoxysilane typically differs by at least 4° C., alternatively at least 10° C., alternatively 10° C. to 200° C. from that of the aminoalkylalkoxysilane. The difference in boiling point allows for the separation of the N-substituted aminoalkylalkoxysilane and the aminoalkylalkoxysilane.

Examples of the N-substituted aminoalkylalkoxysilanes that can be produced by the method include, but are not limited to, N-substituted aminoalkylalkoxysilanes having the following formula: $H_2NCH_2CH_2NH(CH_2)_3Si(OCH_3)_3$, $H_2NCH_2CH_2NH(CH_2)_3Si(CH_3)(OCH_3)_2$, $H_2NCH_2CH_2NH(CH_2)_3Si(CH_3)_2(OCH_3)$, $H_2NCH_2CH_2NH(CH_2)_3Si(OCH_2CH_3)_3$, $H_2NCH_2CH_2NH(CH_2)_3Si(CH_3)(OCH_2CH_3)_2$, $H_2NCH_2CH_2NH(CH_2)_3Si(CH_3)_2(OCH_2CH_3)$, $H_2N(CH_2)_2NH(CH_2)_2NH(CH_2)_3Si(OCH_3)_3$, $H_2N(CH_2)_2NH(CH_2)_2NH(CH_2)_3Si(CH_3)(OCH_3)_2$, $H_2N(CH_2)_2NH(CH_2)_2NH(CH_2)_3Si(CH_3)_2(OCH_3)$, $H_2N(CH_2)_2NH(CH_2)_2NH(CH_2)_3Si(OCH_2CH_3)_3$, $H_2N(CH_2)_2NH(CH_2)_2NH(CH_2)_3Si(CH_3)(OCH_2CH_3)_2$, $H_2N(CH_2)_2NH(CH_2)_2NH(CH_2)_3Si(CH_3)_2(OCH_2CH_3)$, $C_6H_{11}NH(CH_2)_3Si(OCH_3)_3$, $C_6H_{11}NH(CH_2)_3Si(CH_3)(OCH_3)_2$, $C_6H_{11}NH(CH_2)_3Si(CH_3)_2(OCH_3)$, $C_6H_{11}NH(CH_2)_3Si(OCH_2CH_3)_3$, $C_6H_{11}NH(CH_2)_3Si(CH_3)(OCH_2CH_3)_2$, $C_6H_{11}NH(CH_2)_3Si(CH_3)_2(OCH_2CH_3)$, $C_6H_5NH(CH_2)_3Si(OCH_3)_3$, $C_6H_5NH(CH_2)_3Si(CH_3)(OCH_3)_2$, $C_6H_5NH(CH_2)_3Si(CH_3)_2(OCH_3)$, $C_6H_{11}NH(CH_2)_3Si(OCH_2CH_3)_3$, $C_6H_5NH(CH_2)_3Si(CH_3)(OCH_2CH_3)_2$, $C_6H_5NH(CH_2)_3Si(CH_3)_2(OCH_2CH_3)$, $C_6H_5CH_2NH(CH_2)_3Si(OCH_3)_3$, $C_6H_5CH_2NH(CH_2)_3Si(CH_3)(OCH_3)_2$, $C_6H_5CH_2NH(CH_2)_3Si(CH_3)_2(OCH_3)$, $C_6H_5CH_2NH(CH_2)_3Si(OCH_2CH_3)_3$, $C_6H_5CH_2NH(CH_2)_3Si(CH_3)(OCH_2CH_3)_2$, $C_6H_5CH_2NH(CH_2)_3Si(CH_3)_2(OCH_2CH_3)$,

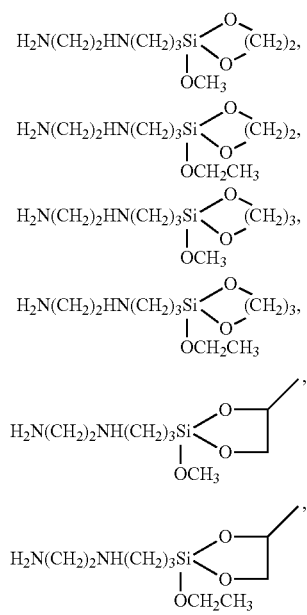

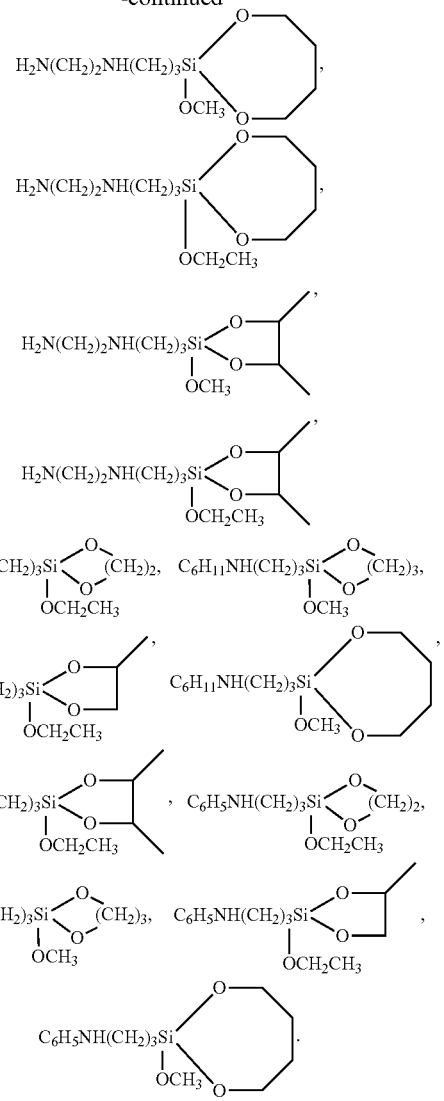

The method of the invention has several benefits. The method allows for the production and isolation of N-substituted aminoalkylalkoxysilanes and aminoalkylalkoxysilanes of high purity. The method consumes the haloalkylalkoxysilane in less time and, therefore, using less energy than reacting the haloalkylalkoxysilane with ammonia alone. The method can produce N-substituted aminoalkylalkoxysilanes that are commercially useful and that are separated easily from the aminoalkylalkoxysilane by, for example, distillation. The method reduces the production of the bis and tris-amine by-product, and the method reduces the overall production time of high purity aminoalkylalkoxysilane. It is not intended that every embodiment of the invention herein described is required to exhibit every benefit discussed.

The aminoalkylalkoxysilane products of the present method can be used as coupling agents for thermoset and thermoplastic resins with glass or mineral fillers.

EXAMPLES

The following examples are included to demonstrate embodiments of the invention. It should be appreciated by those of skill in the art that the techniques disclosed in the examples which follow represent techniques discovered by the inventors to function in the practice of the invention, and thus can be considered to constitute modes for its practice. However, those of skill in the art should, in light of the present disclosure, appreciate that many changes can be made in the specific embodiments which are disclosed and still obtain a like or similar result without departing from the spirit and scope of the invention. All percentages are in wt. %.

Example 1 is provided to demonstrate the entire method including the reaction of ammonia and the haloalkylalkoxysilane to form the mixture of the aminoalkylalkoxysilane, unreacted haloalkylalkoxysilane, and ammonium halide. The remaining examples are provided to demonstrate the method after the reaction between ammonia and the haloalkylalkoxysilane has been stopped and the reactor vented to provide a mixture of aminoalkylalkoxysilane, unreacted haloalkylalkoxysilane, and ammonium halide. The following table of acronyms and abbreviations used in the examples is provided for reference.

TABLE 1

| Abbreviations and acronyms used in the examples. | |
|---|---|
| Gas chromatography with a flame ionization detector | GC-FID |
| Gas chromatography-mass spectrometry | GS-MS |
| Chloropropyltriethoxysilane | CPTES |
| Ethylenediamine | EDA |
| 3-Aminopropyltriethoxysilane | APTES |
| Cyclic APTES | C-APTES |
| phenylaminopropyltriethoxysilane ($C_6H_5NH(CH_2)_3Si(OEt)_3$) | P-APTES |
| EtO, or OEt | ethoxy group |
| Me | methyl group |
| X-ray Fluorescence | XRF |
| gram(s) | g |
| N/D | No data |
| Parts per million (by weight unless otherwise indicated) | ppm |
| Standard cubic centimeters per minute | scc/min |
| DA | N-aminoethyl-3-aminopropyltriethoxysilane |
| C-DA | Cyclic, N-aminoethyl-3-aminopropyldiethoxysilane |
| Temperature | temp. |
| EDA | ethylenediamine |
| μ | micro |

Gas chromatography was performed using a Hewlett Packard 6890 gas chromatograph equipped with a 30.0 m×320.00 μm capillary column (model number Agilent 19091J-413) operated from 40-450° C. and a flame ionization detector (FID) detector.

Chloride was determined by potentiometric titration with silver nitrate using a silver indicating electrode and a silver-silver chloride double junction reference electrode.

Example 1

A 2 liter Parr high-pressure reactor was loaded with 151 g of CPTES and 430 grams of ammonia. The reactor temperature was brought to then maintained between 80 and 100° C. for 3 hours and then cooled to room temperature and vented by bleeding off ammonia before all of the CPTES was consumed. The product was mixed with 161 grams hexane and then with an 83 gram hexane rinse poured into a pressure-filtration vessel and pressure-filtered with nitrogen. The filtered product was mixed with 176 grams EDA in a 1 liter flask and allowed to react at room temperature for two days. After the reaction, two phases were observed, separated, pressure filtered and analyzed by GC-FID. The top translucent, white phase was 337 grams of mostly hexane and silanes, while the foggy, straw-colored bottom layer was 140 grams of primarily EDA and EDA salts. No CPTES was detected. This example demonstrates that EDA will react residual CPTES.

Example 2

A 2 liter flask was loaded with 298.85 grams APTES, 36.12 grams CPTES, and 180.30 grams of EDA. The mixture was refluxed at 115° C. for 2 hours. The product separated into two phases: a 397 gram top phase and a 25 gram bottom phase. The bottom and top phases were analyzed by GC-FID and contained a small amount of DA and no CPTES. X-ray fluorescence (XRF) analysis confirmed that the bottom phase contained the hydrochloride salts. This example replicates example 1 without conducting the ammonia-CPTES reaction step and demonstrates that EDA would react to consume residual CPTES.

Example 3

A 2 liter flask was loaded with 298.85 grams APTES, 36.12 grams CPTES, and 180.30 grams of EDA. The mixture was then refluxed at 115° C. for 2 hours. A 460 gram product phase and a 30 gram salt phase were obtained. The product phase was vacuum stripped at about 2 in Hg absolute pressure. By GC-FID testing, Cut 1 and Cut 2 contained primarily EDA, and Cut 3 contained mostly APTES and was a hazy, yellow color. Most of the material was taken overhead as Cut 4, which was light amber in color and almost 90% APTES. A small amount of amber-colored material, which contained slightly more diamine than Cut 4, remained in the pot. The stripping results are summarized in Table 2. There was no C-DA or CPTES detected.

TABLE 2

| Results of product strip. | | | | | | | |
|---|---|---|---|---|---|---|---|
| Sample | Mass (g) | Pot Temp (° C.) | EtOH (%) | EDA (%) | C-APTES (%) | APTES (%) | DA (%) |
| Cut 1 | 88 | 25-60 | 5.40 | 94.43 | 0.00 | 0.00 | 0.00 |
| Cut 2 | 35 | 60-85 | 4.26 | 95.74 | 0.00 | 0.00 | 0.00 |
| Cut 3 | 52 | 85-140 | 2.08 | 11.20 | 0.00 | 75.32 | 5.75 |
| Cut 4 | 204 | 140-147 | 0.78 | 0.46 | 0.00 | 88.07 | 5.91 |
| Pot | 37 | N/A | 0.60 | 0.00 | 2.26 | 68.51 | 13.75 |

Cut 3, Cut 4, and the pot material were loaded into a 1 liter reaction flask equipped with a nitrogen sweep, a 15 in Vigreux-style distillation column, and a total condenser, and fractional distillation was conducted. The results of the fractional distillation are summarized in Table 3. Seven overhead cuts were collected, and 20 grams of viscous, dark amber material remained in the flask. The first 5 cuts were analyzed by GC-FID and found to contain over 98% APTES (including cyclic). EDA and CPTES were not detected.

TABLE 3

Results of fractional distillation of Cut 3, Cut 4, and pot material.

| Sample | Mass (g) | Pot Temp (° C.) | EtOH (%) | C-APTES (%) | APTES (%) | C-DA (%) | DA (%) |
|---|---|---|---|---|---|---|---|
| Cut 1 | 24 | 25-155 | 0.30 | 0.00 | 98.3 | 0.31 | 0.49 |
| Cut 2 | 61 | 155-157 | 0.00 | 2.18 | 96.94 | 0.29 | 0.59 |
| Cut 3 | 19 | 157-159 | 0.00 | 5.23 | 93.77 | 0.00 | 1.00 |
| Cut 4 | 21 | 159-162 | 0.00 | 7.17 | 91.52 | 0.00 | 1.31 |
| Cut 5 | 42 | 162-168 | 0.00 | 7.90 | 90.36 | 0.00 | 1.74 |
| Cut 6 | 17 | 168-175 | 0.00 | 10.77 | 84.64 | 0.00 | 4.09 |
| Cut 7 | 21 | 175-179 | 0.00 | 8.84 | 75.48 | 0.00 | 12.51 |

This example demonstrates that residual CPTES will react with EDA and be consumed, and the resulting APTES and N-aminoethyl-3-aminopropyltriethoxysilane can be separated by fractional distillation to give APTES of purity greater than 98%.

Example 4

Using the same reaction apparatus described in example 3, 232 grams aminopropyltriethoxysilane, 108 grams of CPTES, and 270 grams of EDA were refluxed for 2 hours at 115° C. After two hours, two phases formed. The top, product-phase, was 464 grams, and the bottom phase was 106 grams. Four product layer samples were then mixed with various levels of hexane, as shown in Table 4. Each sample with hexane added was allowed to phase separate.

The time required for phase separation decreased, and the size of the waste layer increased as the hexane concentration in the samples increased. The top phase of each sample was filtered using a 0.45 micrometer syringe filter and tested for chloride using a potentiometric titration with silver nitrate. The results are listed in Table 4.

TABLE 4

Samples for salt precipitation.

| Sample | Hexane (g) | Product (g) | Chloride (ppm) |
|---|---|---|---|
| A | 4.86 | 15.15 | 387 |
| B | 6.96 | 13.04 | 196 |
| C | 10.06 | 9.94 | 42.9 |
| D | 13.43 | 6.58 | 25.6 |

The four filtered samples were then mixed with 200 grams of the product layer and hexane to give a mass fraction hexane of 0.5, and allowed to separate. The EDA/EDA-HCl waste was phase separated and discarded, and the product phase was pressure filtered and distilled. The product-hexane phase was added to the same distillation apparatus used in example 3 and distilled at 2 in Hg absolute pressure. Cut 1 and 2 contained primarily hexane and EDA. Cut 3 was returned to the pot, the nitrogen sweep was reduced to 100 scc/min, and distillation continued. The distillation results for cuts 4-10 are in Tables 5 and 6. No CPTES was detected by GC-FID. About 20 grams of viscous, caramel-colored material was left in the pot at the end of the distillation.

TABLE 5

Product distillation results.

| Sample | Mass (g) | Pot Temp (° C.) | Overhead Temp (° C.) | EtOH (%) | EDA (%) |
|---|---|---|---|---|---|
| Cut 4 | 7 | 72-144 | 50 | 9.04 | 19.48 |
| Cut 5 | 24 | 144-148 | 130 | 0.11 | 1.16 |
| Cut 6 | 14 | 148-149 | 127 | 0.00 | 0.00 |
| Cut 7 | 22 | 144-160 | 128 | 0.00 | 0.00 |
| Cut 8 | 10 | 160-171 | 128-170 | 0.00 | 0.00 |
| Cut 9 | 19 | 171-200 | 133-140 | 0.00 | 0.00 |
| Cut 10 | 22 | 200-231 | 120-158 | 0.00 | 0.00 |

TABLE 6

Product distillation results continued.

| Sample | C-APTES | APTES | C-DA | DA |
|---|---|---|---|---|
| Cut 4 | 0.74 | 67.66 | 0.25 | 1.87 |
| Cut 5 | 0.05 | 96.43 | 0.37 | 1.75 |
| Cut 6 | 1.14 | 95.69 | 0.33 | 2.11 |
| Cut 7 | 6.09 | 90.75 | 0.33 | 2.84 |
| Cut 8 | 0.00 | 90.15 | 0.24 | 8.64 |
| Cut 9 | 2.52 | 59.07 | 0.78 | 35.12 |
| Cut 10 | 0.00 | 28.79 | 0.00 | 57.55 |

Example 5

A 3 L flask equipped with an agitator, a reflux condenser, and a nitrogen blanket was loaded with 465 grams APTES, 217 grams CPTES, 6.82 grams ammonium chloride, and 557 grams of EDA. The flask was heated and the contents refluxed at 115° C. for 2 hours. After 2 hours, two phases were formed. Hexane was added incrementally up to a 1:1 mass ratio for a projected 703 g of silane. A 7 gram sample was obtained from the top phase after each hexane addition and titrated for chloride. Between additions, the flask was agitated for 10 minutes and then allowed to separate for 10 minutes. Ionic chloride testing by potentiometric titration with silver nitrate was performed on the unfiltered samples (results in Table 7).

TABLE 7

Chloride results with hexane addition

| Sample | Total Hexane (g) | Chloride (ppm) |
|---|---|---|
| A | 0 | 924.6 |
| B | 70 | 642.3 |
| C | 352 | 129.2 |
| D | 704 | 47.4 |

A product sample after the final hexane addition and separation was syringe-filtered and was found to have 30.3 ppm chloride. After the final hexane addition, the top layer was isolated and stripped using a 5 liter flask with an estimated 100 scc/min nitrogen sweep and 15 inch Vigreux column with total condenser and at 4 in Hg absolute pressure. The fractions were collected in a receiver and cold traps and tested by GC-FID. The first three fractions collected at room temperature, 93° C., and 132° C. consisted of primarily hexane, EDA and a small amount of silanes. After these first three fractions, the pot size was reduced to 1 liter, and the pot temperature was increased to 200° C. with a corresponding overheads temperature of around 165° C. A total of 565 grams of clear, water-white material was collected in the receiver leaving about 22 grams of gel in the pot.

The 565 grams of stripped material was loaded into a 1 liter flask outfitted with a 10-tray distillation column and a reflux-controlling head with total condenser. The apparatus was inerted with nitrogen. Fractional distillation was then conducted at 10-20 mmHg absolute pressure. Nine distillation cuts were weighed and analyzed by GC-FID. The results are in Table 8. No CPTES was detected.

TABLE 8

Fractional distillation of stripped material.

| Sample | Mass (g) | Pot Temp (° C.) | Overhead Temp (° C.) | C-APTES (%) | APTES (%) | C-DA (%) | DA (%) |
|---|---|---|---|---|---|---|---|
| Cut 1 | 16 | 25-130 | 110 | 0.00 | 94.28 | 0.42 | 0.00 |
| Cut 2 | 62 | 130-132 | 110 | 1.43 | 95.34 | 0.41 | 0.00 |
| Cut 3 | 88 | 132 | 110 | 0.36 | 96.58 | 0.38 | 0.00 |
| Cut 4 | 50 | 132-137 | 110-113 | 1.49 | 96.62 | 0.38 | 0.00 |
| Cut 5 | 77 | 137-145 | 108-111 | 1.37 | 97.67 | 0.31 | 0.00 |
| Cut 6 | 60 | 145-162 | 106-116 | 4.58 | 94.48 | 0.20 | 0.00 |
| Cut 7a* | 71 | 162-176 | 130-152 | 0.62 | 49.48 | 11.40 | 35.23 |
| Cut 7b* | 3 | 162-176 | 130-152 | N/D | N/D | N/D | N/D |
| Cut 8* | 55 | 176-185 | 140-156 | 0.00 | 6.42 | 18.11 | 69.13 |
| Cut 9 | 16 | 185-191 | 151 | 0.00 | 0.92 | 14.67 | 79.30 |

*white crystals were observed in these samples. The crystals were isolated as cut 7b, dissolved in hexane and analyzed by GC-MS to determine their composition, which was found to be DA and DA disoloxane.

Example 6

A 1 L, 3 neck, round-bottom flask was loaded with 164.70 g (0.744 g-mol) APTES and 59.49 g (0.247 g-mol) CPTES. The flask was heated to 80° C., and then 215.73 g cyclohexylamine was added over a 45 minute period through an addition funnel. The flask temperature was maintained between 75° C. and 80° C. for two hours, and a Liebig condenser was used to prevent loss of material through evaporation. The flask was cooled to room temperature, and a sample was retrieved. Hexane was added to promote phase separation, since the sample was mostly solid with a little liquid. The sample was analyzed using GC. The composition of the sample showed that the only a small amount (15-20%) of the CPTES was converted to cyclohexylaminopropyltriethoxysilane. This experiment demonstrated that the rate of reaction between cyclohexylamine and CPTES is slow at 75-80° C.

Example 7

The same apparatus as in example 6 was loaded with 161.18 g (0.728 g-mol) APTES and 62.04 g (0.258 g-mol) CPTES. The flask was heated to 125° C.; then 220.07 g (2.22 g-mol) cyclohexylamine was added. The temperature was maintained at 125° C. for two hours then allowed to cool. The flask was then heated to 110° C.-115° C., and a sample was retrieved. Hexane was added and another sample was taken, to which NaOEt was added. The GC chromatograms showed that 8% of cyclohexylaminopropyltriethoxysilane product formed, and that it may have initially been converted to a cyclic silazane or formed a salt. The GC testing indicated that all CPTES was consumed.

Example 8

The same apparatus as in example 6 was loaded with 191.16 g (0.864 g-mol) APTES and 67.06 g (0.278 g-mol) CPTES. The flask was heated to 140° C., then 254.98 g (2.78 g-mol) aniline was added slowly over a 30 minute period. After the addition was complete, the flask temperature was maintained at 140° C. for two hours. The flask was cooled to 80° C. when a sample was extracted for GC measurements. The GC chromatogram showed the pot sample to contain 70% aniline, 18% APTES, and 5% cyclohexylaminopropyl-triethoxysilane. CPTES was completely consumed.

The flask and contents were heated twice more at higher temperatures. The flask was heated for two hours at 150° C. and then two hours at 170° C. Samples were retrieved after the heating at 150° C. and after the heating at 170° C. for GC measurements. No hexane was added. A product peak was observed in all three GC readings, as well as a peak pointing to a salt or cyclic product. Sodium ethylate (NaOEt) was added to the sample heated up to 170° C. to free the cyclic and salt forms of the chemicals in the sample and convert them into their non-salt or non-cyclic form. The peak was confirmed to be a salt/cyclic product. There was no observable difference in the amount of product in each sample. This example shows that aniline will react with unreacted CPTES to form a product and consumer CPTES.

Example 9

The same apparatus as in example 6 was loaded with 183.34 g APTES and 69.48 g CPTES. The flask was brought to 145° C., and 254.81 g of aniline were added to the flask over a 15-30 minute period. The temperature was maintained for two hours, and a sample was taken for GC measurements. Another sample was taken and mixed with NaOEt. GC-FID analysis showed the sample contained 67% aniline, 20% APTES, and 5% cyclohexylaminopropyltriethoxysilane. CPTES was completely consumed.

Example 10

The product from examples 8 and 9 were combined and distilled in a 1 L 3-neck round bottom flask using a 5 tray Claisen distillation head. The pressure ranged from 5 mmHg to 100 mmHg absolute pressure, and the temperature ranged from 100° C. to 200° C. The aniline and APTES were distilled, leaving the pot with P-APTES. Aniline was easily stripped off, with approximately 90% purity through vacuum distillation at 9.5 mmHg absolute pressure and a pot temperature of 110° C. The APTES was not stripped as easily. At a pressure as low as 13 mmHg absolute pressure and a pot temperature as high as 145° C. a cut containing 90% APTES and C-APTES was obtained. The GC-MS chromatogram of the pot substance showed 4 peaks, identified as P-APTES, P-APTES salt, cyclic P-APTES, cyclic P-APTES salt.

Example 11

Comparative Prophetic Example

This example is prepared by using data from lab and production runs. It is a kinetic model and is only meant to be predictive of actual physical experiments. In a high pressure reactor is combined ammonia and CPTES at a molar ratio of ammonia to CPTES of 35:1. The reactor is heated to and maintained at 85° C. for 13 hours. The conversion of CPTES is predicted to be 94.01% after 4 hrs, 98.54% after 6 hrs., 99.64% after 8 hrs., 99.91% after 10 hrs., 99.98% after 12 hrs., and 99.99% after 13 hrs.

That which is claimed is:

1. A method of preparing an aminoalkylalkoxysilane, the method comprising:
   (i) reacting a haloalkylalkoxysilane having the formula $X(CH_2)_m SiR^1{}_n(OR^1)_{3-n}$ (I) or

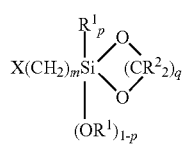

(II)

with ammonia in a high pressure reactor at a temperature from 30 to 200° C. and for an amount of time sufficient to consume from 20 to 99.99% (w/w) of the haloalkylalkoxysilane and form an aminoalkylalkoxysilane, wherein each $R^1$ is independently selected from $C_1$-$C_{10}$ hydrocarbyl, each $R^2$ is independently selected from —H, and $C_1$-$C_4$ hydrocarbyl, m is 1, 2, 3, 4, 5 or 6, n is 0, 1, or 2, p is 0 or 1, q is 2, 3, 4, or 5, and X is halo;
   (ii) venting ammonia from the reactor to give a mixture comprising the aminoalkylalkoxysilane, unreacted haloalkylalkoxysilane, and an ammonium halide; and
   (iii) treating the mixture with a primary amine having a boiling point of at least 115° C. such that the primary amine reacts with the unreacted haloalkylakoxysilane to form an N-substituted aminoalkylalkoxysilane.

2. The method of claim 1 wherein the haloalkylalkoxysilane has the formula $X(CH_2)_m SiR^1{}_n(OR^1)_{3-n}$, wherein each $R^1$ is independently ethyl or methyl, m is 3, n is 0, and X is chloro.

3. The method of claim 1, wherein the haloalkylalkoxysilane is reacted with the ammonia for an amount of time sufficient to consume from 70 to 99.98% (w/w) of the haloalkylalkoxysilane.

4. The method of claim 1, wherein the haloalkylalkoxysilane and ammonia are reacted for from 0.5 hours to 2.5 hours.

5. The method of claim 1, wherein the ammonia and the haloalkylalkoxysilane are reacted at a gauge pressure from 3400 to 5500 kPa.

6. The method of claim 1, wherein the primary amine has a boiling point from 115 to 400 °C.

7. The method of claim 1, wherein the primary amine has the formula $H_2N(—R^3NH—)_cH$, wherein each $R^3$ is independently hydrocarbylene and c is 1, 2, 3 or 4, or $H_2NR^4$, wherein $R^4$ is hydrocarbyl.

8. The method of claim 1 wherein the mixture is treated with the primary amine at a temperature from 50 to 150 °C.

9. The method of claim 1 wherein the mixture is treated with the primary amine for from 5 minutes to 2.5 hours.

10. The method of claim 1 wherein the mixture is treated with from 0.5 to 40 moles of primary amine per mole of haloalkylalkoxysilane in the mixture.

11. The method of claim 1, the method further comprising recovering the aminoalkylalkoxysilane and the N-substituted aminoalkylalkoxysilane.

12. The method of claim 1, the method further comprising removing the ammonium halide.

13. The method of claim 1, further comprising separating the aminoalkylalkoxysilane and the N-substituted aminoalkylalkoxysilane.

14. The method of claim 1 wherein the aminoalkylalkoxysilane has the formula $H_2N(CH_2)_m SiR^1{}_n(OR^1)_{3-n}$ (III) or

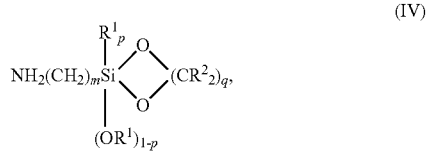

wherein each $R^1$ is independently selected from $C_1$-$C_{10}$ hydrocarbyl, each $R^2$ is independently selected from —H and $C_1$-$C_4$ hydrocarbyl, m is 1, 2, 3, 4, 5 or 6, n is 0, 1 or 2, p is 0 or 1, and q is 2, 3, 4 or 5.

15. The method of claims 1, wherein the N-substituted aminoalkylalkoxysilane has the formula $YNH(CH_2)_m SiR^1{}_n (OR^1)_{3-n}$ (V) or

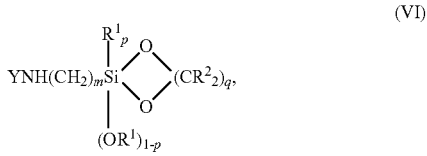

wherein each $R^1$ is independently selected from $C_1$-$C_{10}$ hydrocarbyl, each $R^2$ is independently selected from —H and $C_1$-$C_4$ hydrocarbyl, m is 1, 2, 3, 4, 5, or 6, p is 0 or 1, q is 2, 3, 4, or 5 and Y is —$R^3NH(R^3NH)_cH$ or $R^4$, wherein $R^3$ is hydrocarbylene, $R^4$ is hydrocarbyl, and c is 0, 1, 2, or 3.

* * * * *